US010492710B2

(12) United States Patent
Wang et al.

(10) Patent No.: US 10,492,710 B2
(45) Date of Patent: Dec. 3, 2019

(54) SYSTEM AND METHOD FOR SPECTROSCOPIC MAGNETIC RESONANCE FINGERPRINTING

(71) Applicant: Case Western Reserve University, Cleveland, OH (US)

(72) Inventors: Charlie Y. Wang, Cleveland, OH (US); Mark A. Griswold, Shaker Heights, OH (US); Xin Yu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 275 days.

(21) Appl. No.: 15/589,295

(22) Filed: May 8, 2017

(65) Prior Publication Data
US 2017/0319098 A1  Nov. 9, 2017

Related U.S. Application Data

(60) Provisional application No. 62/332,494, filed on May 6, 2016.

(51) Int. Cl.
*A61B 5/055* (2006.01)
*G01R 33/46* (2006.01)
(Continued)

(52) U.S. Cl.
CPC .......... *A61B 5/055* (2013.01); *A61B 5/14546* (2013.01); *A61B 5/4866* (2013.01);
(Continued)

(58) Field of Classification Search
CPC ... A61B 5/055; A61B 5/14546; A61B 5/4866; A61B 2576/00; G01R 33/4625; G01R 33/448; G01R 33/465
See application file for complete search history.

(56) References Cited

U.S. PATENT DOCUMENTS

| 8,723,518 | B2 | 5/2014 | Seiberlich | |
| 2005/0059881 | A1* | 3/2005 | Balaban | A61B 5/055 600/420 |

(Continued)

OTHER PUBLICATIONS

Alger JR, et al. In vivo phosphorus-31 nuclear magnetic resonance saturation transfer studies of adenosinetriphosphatase kinetics in *Saccharomyces cerevisiae*. Biochemistry 1982;21:2957-63.

(Continued)

*Primary Examiner* — Patrick Assouad
*Assistant Examiner* — Haidong Zhang
(74) *Attorney, Agent, or Firm* — Quarles & Brady LLP

(57) ABSTRACT

The present disclosure relates to a method for performing phosphorous-31 spectroscopic magnetic resonance fingerprinting (MRF). The method comprises performing a pulse sequence using a series of varied sequence blocks to a volume in a subject where the volume contains phosphate metabolites. A series of signal evolutions are acquired from the volume in the subject to form MRF data. The MRF data is then compared to simulated MRF signal to determine parameters associated with phosphate metabolites and the chemical exchange rates between these metabolites. These parameters and exchange rates can be used in diagnosing a metabolic disorder in a subject.

20 Claims, 3 Drawing Sheets

(51) Int. Cl.
- A61B 5/00 (2006.01)
- A61B 5/145 (2006.01)
- G01R 33/34 (2006.01)
- G01R 33/465 (2006.01)
- G01R 33/385 (2006.01)
- G01R 33/44 (2006.01)

(52) U.S. Cl.
CPC ....... *G01R 33/465* (2013.01); *G01R 33/4625* (2013.01); *A61B 2576/00* (2013.01); *G01R 33/448* (2013.01)

(56) References Cited

U.S. PATENT DOCUMENTS

| | | | |
|---|---|---|---|
| 2015/0141804 A1* | 5/2015 | Rooney | A61B 5/0037 600/419 |
| 2015/0262389 A1* | 9/2015 | Li | G01T 1/1603 382/131 |
| 2015/0301141 A1 | 10/2015 | Griswold | |

OTHER PUBLICATIONS

Balaban RS, et al. In vivo flux between phosphocreatine and adenosine triphosphate determined by two-dimensional phosphorous NMR. J Biol Chem. 1983;258(21):12787-12789.

Balaban RS, et al. Interpretation of 31P NMR saturation transfer experiments: what you can't see might confuse you. Focus on Standard magnetic resonance-based measurements of the Pi?ATP rate do not index the rate of oxidative phosphorylation in cardiac and skeletal muscles. Am. J. Physiol. Cell Physiol. 2011;301:C12-5.

Bashir A, et al. Reproducibility of creatine kinase reaction kinetics in human heart: a (31) P time-dependent saturation transfer spectroscopy study. NMR Biomed. 2014;27(6):663-671.

Befroy DE, et al. 31P-magnetization transfer magnetic resonance spectroscopy measurements of in vivo metabolism. Diabetes 2012;61:2669-78.

Befroy DE, et al. Impaired mitochondrial substrate oxidation in muscle of insulin-resistant offspring of type 2 diabetic patients. Diabetes 2007;56:1376-81.

Befroy DE, et al. Increased substrate oxidation and mitochondrial uncoupling in skeletal muscle of endurance-trained individuals. Proc. Natl. Acad. Sci. U. S. A. 2008;105:16701-6.

Bieri O, et al. Fundamentals of balanced steady state free precession MRI. J. Magn. Reson. Imaging 2013;38:2-11.

Bittl JA, et al. Contractile failure and high-energy phosphate turnover during hypoxia: 31P-NMR surface coil studies in living rat. Circ Res. 1987;60(6):871-878.

Bittl JA, et al. Rate equation for creatine kinase predicts the in vivo reaction velocity: 31P NMR surface coil studies in brain, heart, and skeletal muscle of the living rat. Biochemistry 1987;26:6083-90.

Bloch F. Generalized theory of relaxation. Phys. Rev. 1957;105:1206-1222.

Bogner W, et al. Assessment of (31)P relaxation times in the human calf muscle: a comparison between 3 T and 7 T in vivo. Magn Reson Med. 2009;62(3):574-582.

Bottomley PA, et al. Four-Angle Saturation Transfer ( FAST ) Method for Measuring Creatine Kinase Reaction Rates In Vivo. 2002;863:850-863.

Bresnen A, et al. Brain High-Energy Phosphates and Creatine Kinase Synthesis Rate under Graded Isoflurane Anesthesia?: An In Vivo 31 P Magnetization Transfer Study at 11 . 7 Tesla. 2015;730:726-730.

Brindle KM, et al. 31P NMR magnetization-transfer measurements of ATP turnover during steady-state isometric muscle contraction in the rat hind limb in vivo. Biochemistry 1989;28:4887-93.

Brown TR, et al. 31P nuclear magnetic resonance measurements of ATPase kinetics in aerobic *Escherichia coli* cells. Proc. Natl. Acad. Sci. U. S. A. 1977;74:5551-3.

Buonincontri G, et al. Three-dimensional MR fingerprinting with simultaneous B1 estimation. MRM_submitted 2015;00:1-9.

Chen W, et al. Increase of creatine kinase activity in the visual cortex of human brain during visual stimulation: a 31P magnetization transfer study. Magn Reson Med. 1997;38(4):551-557.

Chen Y, et al. MR Fingerprinting for Rapid Quantitative Abdominal Imaging. Radiology. 2016;279(1):278-286.

Choi CS, et al. Paradoxical effects of increased expression of PGC-1alpha on muscle mitochondrial function and insulin-stimulated muscle glucose metabolism. Proc. Natl. Acad. Sci. U. S. A. 2008;105:19926-31.

Christen T, et al. MR vascular fingerprinting: A new approach to compute cerebral blood volume, mean vessel radius, and oxygenation maps in the human brain. Neuroimage 2014;89:262-70.

Degani H, et al. Kinetics of creatine kinase in heart: a 31P NMR saturation- and inversion-transfer study. Biochemistry 1985;24:5510-6.

Du F, et al Efficient in vivo 31P magnetization transfer approach for noninvasively determining multiple kinetic parameters and metabolic fluxes of ATP metabolism in the human brain. Magn. Reson. Med. 2007;57:103-14.

Gao Y, et al. Preclinical MR fingerprinting ( MRF ) at 7 T?: effective quantitative imaging for rodent disease models. 2015:384-394.

Hamilton JI, et al. MR fingerprinting for rapid quantification of myocardial T1, T2, and proton spin density. Magn Reson Med. 2016;0.

Ingwall JS. Phosphorus nuclear magnetic resonance spectroscopy of cardiac and skeletal muscles. Am J Physiol. 1982;242(5):H729-44.

Jiang Y, et al. MR fingerprinting using fast imaging with steady state precession (FISP) with spiral readout. Magn Reson Med. 2015;74(6):1621-1631.

Jucker BM, et al. 13C/31P NMR assessment of mitochondrial energy coupling in skeletal muscle of awake fed and fasted rats. Relationship with uncoupling protein 3 expression. J. Biol. Chem. 2000;275:39279-86.

Kingsley-Hickman PB, et al. 31P NMR measurement of mitochondrial uncoupling in isolated rat hearts. J Biol Chem. 1990;265(3):1545-1550.

Kingsley-Hickman PB, et al. 31P NMR studies of ATP synthesis and hydrolysis kinetics in the intact myocardium. Biochemistry. 1987;26(23):7501-7510.

Lebon V, et al. Effect of triiodothyronine on mitochondrial energy coupling in human skeletal muscle. J. Clin. Invest. 2001;108:733-737.

Lei H, et al. In vivo 31P magnetic resonance spectroscopy of human brain at 7 T: an initial experience. Magn Reson Med. 2003;49(2):199-205.

Lei H, et al. Measurement of unidirectional P i to ATP flux in human visual cortex at 7 T by using in vivo P magnetic resonance spectroscopy. 2003;100.

Leibfritz D, et al. Magnetization transfer MRS. NMR Biomed. 2001;14(2):65-76.

Leupold J, et al. Fast chemical shift mapping with multiecho balanced SSFP. MAGMA 2006;19:267-73.

Ma D, et al. Magnetic resonance fingerprinting. Nature 2013;495:187-192.

Matthews PM, et al. The steady-state rate of ATP synthesis in the perfused rat heart measured by 31P NMR saturation transfer. Biochem. Biophys. Res. Commun. 1981;103:1052-9.

McConnell HM. Reaction Rates by Nuclear Magnetic Resonance. J. Chem. Phys. 1958;28:430-1.

McFarland EW, et al. Activity of creatine kinase in a contracting mammalian muscle of uniform fiber type. Biophys J. 1994;67(5):1912-1924.

Morrison JF, et al. Isotope exchange studies of the mechanism of the reaction catalyzed by adenosine triphosphate: creatine phosphotransferase. J Biol Chem. 1966;241(3):673-683.

Nabuurs C, et al. 31P saturation transfer spectroscopy predicts differential intracellular macromolecular association of ATP and ADP in skeletal muscle. J Biol Chem. 2010;285(51):39588-39596.

Neubauer S, et al. Myocardial phosphocreatine-to-ATP ratio is a predictor of mortality in patients with dilated cardiomyopathy. Circulation. 1997;96(7):2190-2196.

(56) References Cited

OTHER PUBLICATIONS

Neubauer S, et al. Velocity of the creatine kinase reaction decreases in postischemic myocardium: a 31P-NMR magnetization transfer study of the isolated ferret heart. Circ Res. 1988;63(1):1-15.

Parasoglou P, et al. Three-dimensional mapping of the creatine kinase enzyme reaction rate in muscles of the lower leg. NMR Biomed. 2013;26(9):1142-1151.

Parasoglou P, et al. Three-dimensional saturation transfer 31P-MRI in muscles of the lower leg at 3.0 T. Sci. Rep. 2014;4:5219.

Perry CGR, et al. Methods for assessing mitochondrial function in diabetes. Diabetes 2013;62:1041-53.

Petersen KF, et al. Impaired mitochondrial activity in the insulin-resistant offspring of patients with type 2 diabetes. N. Engl. J. Med. 2004;350:664-71.

Petersen KF, et al. Mitochondrial dysfunction in the elderly: possible role in insulin resistance. Science 2003;300:1140-2.

Portman MA. Measurement of unidirectional P(i)→ATP flux in lamb myocardium in vivo. Biochim. Biophys. Acta 1994;1185:221-7.

Ren J, et al. Exchange kinetics by inversion transfer: Integrated analysis of the phosphorus metabolite kinetic exchanges in resting human skeletal muscle at 7 T. Magn. Reson. Med. 2014;1369:1359-1369.

Robitaille PM, et al. Measurement of ATP synthesis rates by 31P-NMR spectroscopy in the intact myocardium in vivo. Magn Reson Med. 1990;15(1):8-24.

Rodgers CT, et al. Human cardiac (31) P magnetic resonance spectroscopy at 7 tesla. Magn. Reson. Med. 2014;72:304-15.

Schar M, et al. Triple repetition time saturation transfer (TRiST) 31P spectroscopy for measuring human creatine kinase reaction kinetics. Magn Reson Med. 2010;63(6):1493-1501.

Schar M, et al. Two repetition time saturation transfer (TwiST) with spill-over correction to measure creatine kinase reaction rates in human hearts. J Cardiovasc Magn Reson. 2015;17(1):70.

Shoubridge EA, et al. 31p NMR saturation transfer measurements of the steady state rates of creatine kinase and ATP synthetase in the rat brain. FEBS Lett. 1982;140:289-92.

Shoubridge EA, et al. Regulation of creatine kinase during steady-state isometric twitch contraction in rat skeletal muscle. BBA—Mol Cell Res. 1984;805(1):72-78.

Speck O, et al. P Chemical Shift Imaging Using SSFP Methods. 2002;639:633-639.

Thoma WJ, et al. Saturation-transfer studies of ATP-Pi exchange in isolated perfused rat liver. Biochim. Biophys. Acta 1987;893:225-31.

Tusek Jelenc M, et al. Feasibility and repeatability of localized 31 P-MRS four-angle saturation transfer (FAST) of the human gastrocnemius muscle using a surface coil at 7?T. NMR Biomed. 2016;29(1):57-65.

Ugurbil K. Magnetization-transfer measurements of individual rate constants in the presence of multiple reactions. J. Magn. Reson. 1985;64:207-219.

Valkovic L, et al. Time-resolved phosphorous magnetization transfer of the human calf muscle at 3 T and 7 T: a feasibility study. Eur J Radiol. 2013;82(5):745-751.

Van Den Broek, et al. Comparison of in vivo postexercise phosphocreatine recovery and resting ATP synthesis flux for the assessment of skeletal muscle mitochondrial function. AJP Cell Physiol. 2010;299(5):C1136-C1143.

Xiong Q, et al. ATP production rate via creatine kinase or ATP synthase in vivo: a novel superfast magnetization saturation transfer method. Circ Res. 2011;108(6):653-663.

Xiong Q, et al. ATP Production Rate via Creatine Kinase or ATP Synthase. 2011:653-663.

Xiong Q, et al. Novel strategy for measuring creatine kinase reaction rate in the in vivo heart. Am. J. Physiol. Heart circ. Physiol. 2009;297:H1010-9.

Yerby B, et al. Insulin-stimulated mitochondrial adenosine triphosphate synthesis is blunted in skeletal muscles of high-fat-fed rats. Metabolism. 2008;57:1584-1590.

\* cited by examiner

SYSTEM AND METHOD FOR SPECTROSCOPIC MAGNETIC RESONANCE FINGERPRINTING

CROSS-REFERENCE TO RELATED APPLICATIONS

This application claims the benefit of U.S. Provisional Patent Application Ser. No. 62/332,494 filed May 6, 2016.

STATEMENT REGARDING FEDERALLY SPONSORED RESEARCH

This invention was made with government support under the grant(s) EB007509, GM007250, HL073315, HL124894, HL126215, and TR000441 awarded by the National Institutes of Health. The government has certain rights in the invention.

BACKGROUND

Characterizing tissue species using nuclear magnetic resonance ("NMR") can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting ("MRF"), which is described, as one example, by D. Ma, et al., in "Magnetic Resonance Fingerprinting," Nature, 2013; 495(7440): 187-192.

Conventional magnetic resonance spectroscopy ("MRS") offers a unique opportunity to noninvasively characterize metabolic profiles in a vast array of pathologies due to its chemical specificity. Phosphorus-31 ($^{31}P$) MRS has been used extensively to assess the energetics of living tissues. In addition to measuring the concentrations of phosphate metabolites involved in tissue metabolism, $^{31}P$ magnetization transfer (MT) techniques have been developed and successfully applied to the quantification of phosphocreatine (PCr) synthesis rate via creatine kinase in heart, skeletal muscle, and brain. The use of $^{31}MT$-MRS for measurement of ATP turnover has also been explored in vitro in cells and perfused organs, and in vivo in laboratory animals and humans. However, $^{31}P$ MT-MRS has found limited utility due to its long data acquisition time needed to compensate for the low metabolite concentrations.

Strategies for shorter acquisition times have been pursued to partially ameliorate this problem. The first strategy uses a reduced number of spectra acquired under partially relaxed conditions, such as in the four angle saturation transfer (FAST) method, or the triple repetition time saturation transfer (TRiST) method. Reducing the number of acquired spectra is particularly useful in combination with CSI methods for spatially localized measurements. However, because the number of acquired spectra approaches the number of parameters to be estimated, the spectra must be of high SNR to achieve satisfactory robustness. Hence, these methods are limited for inherently low SNR applications.

The second strategy to shorten acquisition times reduces the number of unknown parameters by assuming an intrinsic $T_1$ value for PCr, and includes techniques, such as the two repetition time saturation transfer (TwiST) and $T_1$ Nominal methods. However, while several studies have reported no detectable changes in the $T_1$ of PCr under pathological conditions, this does not guarantee that $T_1$ of PCr remains constant in all pathologies and thus fixing the $T_1$ value may lead to measurement errors. Because of this, $^{31}P$ MT-MRS has only found limited utility in evaluating ATP synthesis, which is the most important step in cellular metabolism.

Thus, it would be desirable to provided additional systems and methods for MRS that overcome the aforementioned deficiencies.

SUMMARY OF THE DISCLOSURE

The present disclosure addresses the aforementioned drawbacks by providing a system and method that shortens the acquisition time and allows for greater flexibility in the pulse sequence design. In one aspect, the present disclosure relates to a method for performing spectroscopic magnetic resonance fingerprinting (MRF). The method includes performing a pulse sequence using a series of varied sequence blocks to a volume in a subject that includes one or more metabolites. Signal evolutions from the volume in the subject are then acquired to form MRF data. The MRF data is compared to an MRF dictionary to characterize the one or more metabolites. Once characterized, at least one metabolite parameter can be determined and used to diagnose a metabolic disorder in the subject.

In another aspect, the method includes performing a pulse sequence using a series of varied sequence blocks to a volume in a subject that includes one or more metabolites. Signal evolutions from the volume in the subject are acquired and positioned within a pass-band to form MRF data. The MRF data is compared to simulated MRF signal to characterize the one or more metabolites. Once characterized, at least one metabolite parameter for the one or more metabolites can be determined.

In one aspect, the present disclosure relates to a spectroscopic magnetic resonance fingerprinting system. The system includes a magnet system configured to generate a polarizing magnetic field about at least a portion of a subject. The system further includes a magnetic gradient system including a plurality of magnetic gradient coils configured to apply at least one magnetic gradient field to the polarizing magnetic field. The system also includes a radio frequency (RF) system configured to apply an RF field to the subject and to receive magnetic resonance signals from the subject using a coil array. The system further comprises a computer system programmed to: control the magnetic gradient system and the RF system to perform a pulse sequence using a series of varied sequence blocks to a volume in a subject, the volume containing one or more metabolites; acquire a series of signal evolutions from the volume in the object to form MRF data, wherein the signal evolutions are positioned in a pass-band; characterize the one more metabolites by comparing the MRF data to an MRF dictionary; and determine at least one metabolite parameter, wherein the at least one metabolite parameter is used to diagnose a metabolic disorder in the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
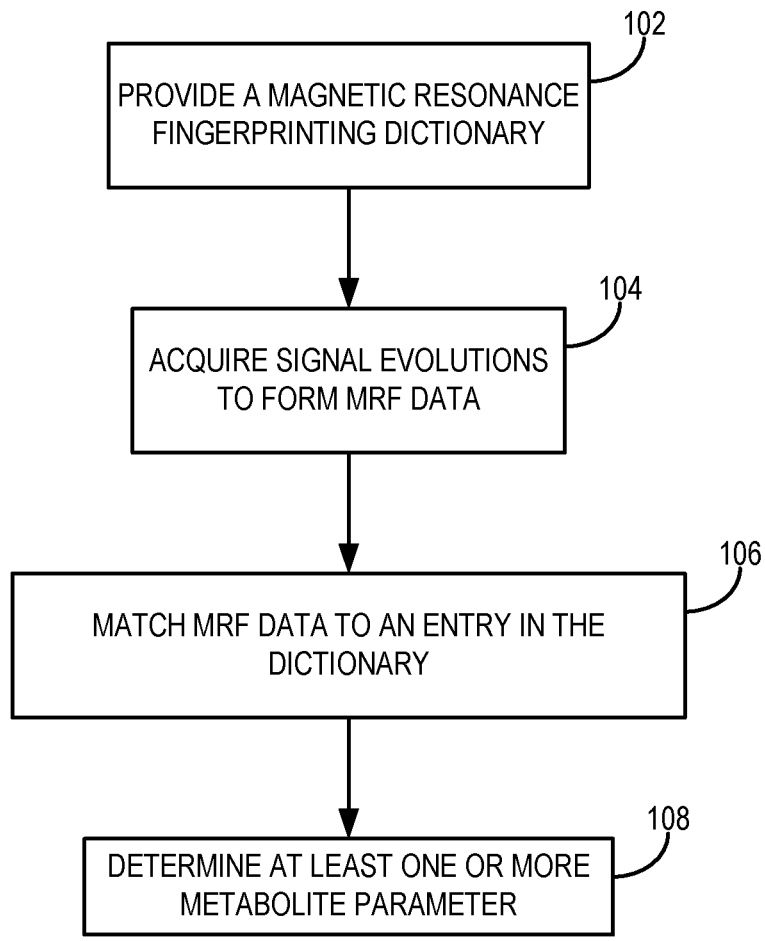
FIG. 1 is a flowchart setting forth the steps of an example method for generating a metabolite parameter using the spectroscopic magnetic resonance fingerprinting ("MRF") system.

Magnetic resonance fingerprinting ("MRF") is a technique that facilitates mapping of tissue or other material properties based on random or pseudorandom measurements of the subject or object being analyzed. In particular, MRF can be conceptualized as employing a series of varied "sequence blocks" that simultaneously produce different signal evolutions in different "resonant species" to which the RF is applied. The term "resonant species," as used herein, may refer to any metabolite that comprises $^1H$, $^{13}C$, and $^{31}P$. Some non-limiting examples of suitable metabolites could include creatine, phosphocreatine, N-acetyl aspartate (NAA), choline, lipids, lactate, myo-insoitol, glutamate, glutamine, and the like. By way of illustration, when radio frequency ("RF") energy is applied to a volume that has both phosphocreatine and ATP, then both the phosphocreatine and ATP will produce a nuclear magnetic resonance ("NMR") signal; however, the "phosphocreatine" represents a first resonant species and the "ATP" represents a second resonant species, and thus the two signals will be different. These different signals from different species can be collected simultaneously over a period of time to collect an overall "signal evolution" for the volume.

The random or pseudorandom measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE"), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, longitudinal relaxation time ($T_1$), transverse relaxation time ($T_2$), main or static magnetic field map ($B_0$), and proton density ($\rho$). MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

In one aspect of the present disclosure, the stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation differences; and $M_0$ is the magnetization in the default or natural alignment to which spins align when placed in the main magnetic field.

While $E_i(T_1,T_2,D)$ is provided as an example, in different situations, the decay term, $E_i(T_1, T_2,D)$, may also include additional terms, $E_i(T_1, T_2,D, \ldots )$ or may include fewer terms, such as by not including the diffusion relaxation, as $E_i(T_1,T_2)$ or $E_i(T_1, T_2, \ldots )$. Also, the summation on "j" could be replace by a product on "j".

The dictionary may store signals described by, $$S_i = R_i E_i(S_{i-1}) \quad (2);$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

Thus, contrary to conventional MRS, MRF uses a data acquisition framework that combines spin history dependence with varied acquisition parameters. To this end, the use of MRF for spectroscopy is counterintuitive when one considers conventional MRS. MRF creates a unique signal evolution pattern, or fingerprint, that does not necessarily reach steady-state. Depending on the acquisition scheme, each fingerprint is uniquely associated with one or more tissue properties such as $T_1$ and $T_2$ relaxation times, perfusion, diffusion, etc. Knowledge of MR physics is used to create a dictionary that includes the range of all feasible fingerprints. Efficient and simultaneous quantification of multiple tissue properties has been demonstrated in $^1$H MRI, with significantly improved data acquisition efficiency and reduced susceptibility to measurement errors. $^{31}$P MT-MRS also involves the estimation of metabolite concentration and the apparent $T_1$ relaxation time ($T_{1app}$), i.e., the chemical exchange modulated $T_1$ relaxation time. Thus, given the multi-parameter nature of $^{31}$P MT-MRS, MRF is particularly well suited for the measurement of phosphorylation rates via both creatine kinase and ATP synthase.

As will be described, the present disclosure provides methods for noninvasively determining metabolic parameters of one or more metabolites that may be utilized to diagnose a metabolic disorder in a subject. When compared with conventional methods such as $^{31}$P magnetization transfer (MT-MRS), spectroscopic magnetic resonance fingerprinting methods as disclosed herein offer faster acquisition times while maintaining accurate quantification of metabolic parameters.

Referring now to FIG. 1, a flowchart is illustrated as setting forth the steps of one non-limiting example for determining the metabolite parameters of the one or more metabolites. As indicated in step 102, an MRF dictionary is provided to a computer system. The MRF dictionary may include signal models, or templates, that have been generated for different acquisition parameters from magnetic resonance signal models. In one aspect, the dictionary may include relative chemical shift and a range of $T_1$ relaxation times for each of the one or more metabolites. The MRF system acquires a series of signal evolutions for the one or more metabolites from a volume in a subject to form MRF data, as indicated in step 104. The signal evolutions may be acquired by performing a pulse sequence using a series of varied sequences blocks to the volume, as described above. The signal evolution for the one or more metabolites can be matched to an entry in the dictionary to characterize the one or more metabolites by comparing the MRF data to an MRF dictionary, as indicated in step 106. Matches are made because each of the one or more metabolites generates a unique signal evolution that may be paired with a dictionary entry when analyzed. Once the one or more metabolites have been matched, the metabolite parameter for the one or more metabolites may be generated, as indicated in step 108. At step 110, the metabolite parameter can then be used to generate a report indicating, for example, the metabolite parameter and other information about the subject to assist with, for example, diagnosing a metabolic disorder in a subject.

In one non-limiting example, a metabolite for the methods disclosed herein may include $^{31}$P chemical moieties such as γATP, PCr, and $P_i$. With determined metabolites, metabolic parameters may be calculated, which may include concentration or chemical exchange rates, such as kinetic rate constant data. These metabolic parameters may also be included in the report at step 100. In some aspects, these metabolic parameters can be used in assessing and diagnosing problems associated with enzyme activity and mitochondrial function by tracking the changes of the metabolic parameters over time. Such data can further be used to track changes in metabolism, aging, and disease. Non-limiting examples of diseases could include monitoring myopathy.

In some aspects, the determination of the metabolite parameters can include quantification of concentration ($M_0$) and longitudinal relaxation time ($T_1$) for the one or more metabolites. In some aspects, the method can include a constant repetition time (TR) and varied flip angles to encode the one or more metabolites. Bloch simulation and template matching approaches are then used to determine metabolic parameters for the metabolites.

In one non-limiting example, the method can include a nonselective hyperbolic secant inversion pulse sequence followed by 512 acquisitions. The 512 acquisitions may further comprise of a series of 16 repeated blocks, with each block comprising 32 acquisitions of linearly ramped (up and down) flip angles ranging from 1.5° to 22.5°. The r.f. pulse train may use hard pulses with alternating phases. A constant TR ranging from 11.2 to 13.5 ms may be used. In some aspects, a constant TR may be used for all the acquisitions. 544 data points may be collected for each acquisition with a dwell time of 11 μs. Total acquisition time of one fingerprint may be about 7 seconds, while each fingerprint acquisition may be followed by an 8 s inter-scan delay.

Similar to a balanced steady-state free precession (bSSFP) acquisition, the use of constant TR leads to a periodic frequency-dependent modulation of signal evolution. In bSSFP, spins with accumulated phase per TR being an odd multiple of n gives rise to steady-state signal void, while the rest of the spins will exhibit relatively uniform and steady-state signal intensity. Although the MRF sequence in the present disclosure may not use constant flip angle or achieves steady-state, these two classes of spins still exist and give rise to very different signal evolutions. As described herein, the first spin class will be defined as located in a "null-band", and the second as located in a "pass-band". In some aspects, adjustment of the carrier frequency and TR allows for placement of a specific resonance at either a pass-band or a null-band.

Figure 2:
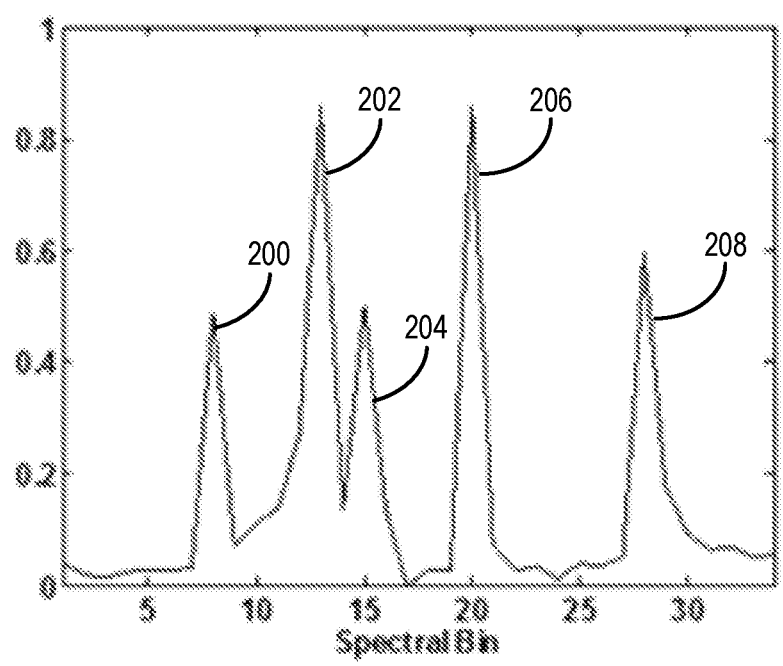
FIG. 2 shows a representative spectrum of the one or more metabolites that have been assigned to a spectral bin based on their unique signal evolutions.

FIG. 2 shows a non-limiting example of a spectrum of metabolites that have been assigned to a spectral bin based on their unique signal evolutions. As shown, line 200 corresponds to a $P_i$ signal, line 202 corresponds to a PCr signal, 204 corresponds to a γATP signal, 206 corresponds to an αATP signal, and 208 corresponds to a βATP signal. In one aspect, the signal evolutions are matched by the vectorization of both the complex Fourier-transformed signal evolutions and dictionary entries using the central and two adjacent spectral bins and then are normalized by their sum-squared magnitude. The vector dot product may be calculated between the acquired signal and each dictionary entry. In some aspects, the $T_1$ value that generates the highest vector dot product with the experimental signal can be used to identify the matched $T_1$. $M_0$ can be subsequently determined by minimizing the error term:

$$\Sigma |S - M_0 D| \qquad (3)$$

where S is the measured signal and D is the matched fingerprint.

In accordance with one aspect of the present disclosure, spectroscopic MRF can be used to provide fast quantification of a metabolite parameter that includes a chemical exchange rate between at least two metabolites. Other metabolite parameters may include a $T_1$ relaxation time and a concentration ratio. In one non-limiting example, the chemical exchange rate is the forward rate constant ($k_f^{CK}$) of ATP synthesis via creatine kinase (CK), and the concentration ratio is PCr-to-ATP ($M_R^{PCr}$).

A method for determining the chemical exchange rate between the metabolites may include an inversion preparation followed by a bSSFP-type acquisition scheme. The acquisition scheme includes a number of acquisition blocks (i.e. 16, 32, 64, etc) and at least two types of acquisition blocks. The two types of acquisition blocks are used to acquire signals for at least two of the metabolites. In one non-limiting example, the two types of acquisition blocks are ACQ-PCr and ACQ-γATP, which are used to acquire signals from PCr and γATP, respectively. A selective saturation block may be used between the two types of acquisition blocks, with the saturation frequency set either at the resonance frequency of γATP (SAT-γATP) or at the frequency contralateral to γATP (SAT-CNTL). In one non-limiting example, a 490-ms saturation block is used between the two types of acquisition blocks. In some aspects, the entire acquisition comprises two modules that employ SAT-CNTL and SAT-γATP, respectively, with the two acquisition blocks for PCr and γATP alternating a number of times (2, 4, 8, 16, etc) in each module.

In some aspects, each of the acquisition blocks includes a train of linearly ramped (up and down) excitations with alternating phase and a constant TR. In one non-limiting example, 10 linearly ramped up and ramped down excitations are used with a constant TR of about 12.8 ms. Selective excitation may be performed with a Gaussian pulse centered at the resonance frequency of the at least two metabolites. In some non-limiting examples, a 4 ms Gaussian pulse is centered at the resonance frequency of PCr and γATP, respectively. Following each excitation, a free induction decay (FID) signal may be collected. The maximum flip angles in the acquisition blocks may be modulated by a sinusoidal envelope. Multiple repetitions may be acquired with no delay, with a single dummy acquisition preceding each series of repetitions.

In one non-limiting experiment, signal evolutions were generated by solving modified Bloch-McConnell equations with two exchanging pools include at least two metabolites. In this non-limiting experiment, the metabolites included PCr, and γATP. Simulation of the signal evolutions included a set number of input parameters. In one non-limiting example, a total of nine input parameters are used such as the forward rate constant of ATP synthesis via CK ($k_f^{CK}$) the concentration ratio of PCr-to-ATP ($M_R^{PCr}$), the $T_1$ and $T_2$ relaxation times and the resonance frequencies (chemical shift) of PCr and γATP ($T_1^{PCr}$, $T_1^{ATP}$, $T_2^{PCr}$, $T_2^{ATP}$, $\omega^{PCr}$, $\omega^{ATP}$), as well as $B_0$ distribution characterized by a linewidth, LW. Given a set of input parameters, spin evolution was simulated in sequential time steps, starting from a fully relaxed initial condition. Excitation was simulated by discretizing the Gaussian shaped RF pulse into a number of instantaneous complex rotations, with the magnitude of the rotation following a Gaussian envelope, and the total rotation summing to the nominal FA. In the non-limiting example, the Guassian shaped RF pulse was discretized into 41 instantaneous complex rotations using the following equations:

$$M^+ = R_x(\alpha_x) R_y(\alpha_y) M^- \quad (4)$$

where $M^-$ and $M^+$ are the magnetization vector before and after the RF pulse, and $R_x(\alpha_x)$ and $R_y(\alpha_y)$ are the rotation matrix about the x- and y-axis with flip angles $\alpha_x$ and $\alpha_y$, respectively, i.e., $$R_x(\alpha_x) = \begin{bmatrix} 1 & & & & \\ & \cos\alpha_x & -\sin\alpha_x & & \\ & \sin\alpha_x & \cos\alpha_x & & \\ & & & \cos\alpha_x & -\sin\alpha_x \\ & & & \sin\alpha_x & \cos\alpha_x \end{bmatrix} \quad (5)$$

$$R_y(\alpha_y) = \begin{bmatrix} \cos\alpha_y & & -\sin\alpha_y & & \\ & 1 & & & \\ \sin\alpha_y & & \cos\alpha_y & & \\ & & & \cos\alpha_y & -\sin\alpha_y \\ & & & 1 & \\ & & & \sin\alpha_y & \cos\alpha_y \end{bmatrix} \quad (6)$$

The phase of each rotation was determined by the excitation frequency. γATP saturation was simulated by instantaneous saturation of γATP magnetization with no direct effect on PCr magnetization. The pulse sequence was simulated sequentially twice to account for the dummy scan. For each simulation, all FID signals were recorded from the bulk transverse magnetization, described by:

$$S(t) = \Sigma_{\Delta\omega_0} W(\Delta\omega_0) M_\perp(t, \Delta\omega_0) \quad (7)$$

where $W(\Delta\omega_0)$ corresponds to weight for a frequency component derived from a Lorentzian lineshape with a linewidth LW:

$$W(\Delta\omega_0) = \frac{LW^2}{(\Delta\omega_0)^2 + LW^2} \quad (8)$$

In some aspects, the dictionary in the MRF framework includes a set of signal evolutions for selected values of the metabolite parameters. In one non-limiting example, four metabolite parameters, namely $k_f^{CK}$, $T_1^{PCr}$, $\omega^{PCr}$, and $M_R^{PCr}$ are varied over their physiologically expected range to generate a dictionary for template matching. In some non-limiting examples, 51 of values for $k_f^{CK}$ may be generated ranging from about 0.3 to 0.55 s$^{-1}$ with a resolution of about 0.005 s$^{-1}$; 20 of values for $T_1^{PCr}$ may be uniformly distributed from about 2.8 to 4.7 s; 11 values for $\omega^{PCr}$ may be generated spanning from about −15 to 15 Hz; 49 for $M_R^{PCr}$ may be uniformly distributed from about 3.0 to 5.4. $\omega^{\gamma ATP}$ for each entry was constrained to ($\omega^{PCr}$−2.4) ppm. The remaining 5 parameters, $T_2^{PCr}$, $T_2^{\gamma ATP}$, $T_1^{\gamma ATP}$, and LW, may be set at about 120 ms, 16 ms, 0.8 s, and 15 Hz respectively based on pilot data. In some aspects, $T_1^{\gamma ATP}$ value may be corrected to compensate for NOE contributions from γATP and γATP.

Returning to the non-limiting example experiment, the metabolite parameter matching step included Fourier transforming the FIDs for the acquired data and simulated dictionary entries. Next, complex-valued data points corresponding to the resonances of at least two of the metabolites were selected. The selected resonances included data points from PCr or γATP resonances. This resulted in a signal evolution showing the evolution of the at least two metabolites. The inner products between the normalized fingerprint and all entries of the normalized dictionary were computed. The dictionary entry that produced the largest magnitude of the inner product was considered to be the best match. From this match, the values of the metabolite parameters were derived. In some aspects, these included $k_f^{CK}$, $T_1^{PCr}$, $\omega^{PCr}$ and $M_R^{PCr}$. Subsequently, other metabolite parameters such as the spin density of γATP ($M_0^{\gamma ATP}$) can be computed as the scale factor between the signal evolution and its matched dictionary entry.

In another aspect, the present disclosure relates to a MRF-based magnetization transfer encoding method (MT-MRF) to quantify at least one metabolic parameter that includes the chemical exchange rate between at least two metabolites. The MT-MRF method utilizes the flexibility of its pulse sequence design to uniquely encode spin parameters related to metabolite exchange. This encoding scheme, combined with a data sampling strategy, leads to efficient quantification of several parameters including rates of chemical exchange, metabolite concentrations, and $T_1$ relaxation time.

In some aspects, the MT-MRF method includes a pulse sequence that comprises three sections. The first section encodes MT flux from a first metabolite to a second metabolite. In some non-limiting examples, the first metabolite comprises γATP and the second metabolite comprises $P_i$. This may be achieved by using a $P_i$-selective hyperbolic secant inversion pulse, followed by data acquisition after a time delay. In some aspects, the time delay may be about 1 second. The second section of the pulse sequence encodes MT flux from the second metabolite to the first metabolite. Continuing the non-limiting example of phosphorous containing metabolites, this may be achieved by applying an adiabatic inversion pulse that is selective to both PCr and γATP prior to data acquisitions. The third section encodes MT flux from a third metabolite and a fourth metabolite through selective saturation of the first metabolite. For example, the third section may encode MT flux via ATP synthase, as well as encoding of MT flux via creatine kinase, through selective γATP saturation.

In some aspects, the data acquisition scheme may sensitize the MT encoding within the sequence. Since MT is primarily encoded in the longitudinal magnetization, the acquisition can form a balance between maximizing SNR and preserving the history of longitudinal magnetization. In some aspects, the data acquisition is arranged into repeated blocks, with each block comprising four RF excitations followed by data acquisition (ACQ). In some aspects, the flip angle of each excitation may be varied. In some aspects, the excitation is a Gaussian-shaped pulses centered at the resonance of the second metabolite. In some aspects, the saturation of the first metabolite may be achieved using a low power continuous wave saturation pulse centered on the resonance of the first metabolite. In some aspects, saturation pulses are applied after the last ACQ of each block.

In one non-limiting example, the flip angle of each excitation was 15°, −30°, 15°, and 0°, respectively, with a TR of 7.7, 7.7, 7.7, and 250 ms, respectively. The Gaussian-shaped pulses were centered at $P_i$ resonance and with a 1.11 ms pulse duration. The first section included 52 blocks with a total of 208 ACQs. The second section included 10 blocks with 40 ACQs. Finally, the third section included 38 blocks with 152 ACQs. Each ACQ has a dwell time of 7.4 μs. A total of 70 data points were acquired, spanning an acquisition window of 5.2 ms. This acquisition scheme led to a spectral resolution of about 192 Hz. About 6 seconds were allowed for partial magnetization recovery before beginning the next signal average. γATP saturation in the third section was achieved using low power continuous wave saturation pulse centered on γATP resonance. Saturation pulses are applied after the last ACQ of each block. To control for possible spillover on $P_i$, the saturation pulses are applied symmetrically downfield of $P_i$ resonance during the first and second sections.

In one non-limiting example, a simulation of $P_i$ magnitude signal using three different rate constant ($k_f^{ATP}$) values was performed. The signal evolution across the three sections of data acquisition showed a biphasic change that reflected the impact of MT flux between $P_i$ and γATP. In the first section, magnetization transfer from γATP to $P_i$ caused $P_i$ signal to recover more quickly than $T_1$ relaxation alone. A faster rate constant led to faster $P_i$ recovery. In second and third sections, the $P_i$ to γATP flux caused $P_i$ signal to decrease, and the decrease occurred more quickly with a faster rate constant. Compared to conventional $T_{1app}$-based MT methods with a monophasic signal evolution, this biphasic signal evolution allowed the estimation of the rate constants to be more robust to $T_1$ estimation errors One example, the signal evolutions for the dictionary were generated by solving the Bloch-McConnell equations based on the chemical exchange system that includes the one or more metabolites. The chemical exchange system included at least three metabolites.

The dictionary model included a set number of parameters. In one non-limiting example, the model included 13 parameters such as the forward rate constants of ATP synthesis via creatine kinase and from $P_i$ ($k_f^{CK}$ and $k_f^{ATP}$), the $T_1$ and $T_2$ relaxation times and the resonance frequencies (chemical shift) of PCr, γATP, and $P_i$ ($T_1^{PCr}$, $T_1^{ATP}$, $T_1^{Pi}$, $T_2^{PCr}$, $T_2^{ATP}$, $T_2^{Pi}$, $\omega^{PCr}$, $\omega^{ATP}$, $\omega^{Pi}$), and the concentration ratios of PCr-to-ATP and $P_i$-to-ATP ($M_R^{PCr}$ and $M_R^{Pi}$).

Also, $B_0$ inhomogeneity was accommodated for by simulating the resonance frequencies for each of the metabolites. Continuing the non-limiting example from above, 51 resonance frequencies were simulated for each metabolite spanning a range of 150 Hz. In some aspects, the bulk signal from each metabolite ($S^X$) was then modeled as the weighted sum of all constituent transverse magnetization ($M_\perp^X$) by:

$$S^X = \Sigma_j W(\omega_j^X) M_\perp^X(\omega_j^W) \tag{9}$$

where $M_\perp^X(\omega_j^X)$ is the signal from metabolite X at a specific resonance frequency $\omega_j^X$ and $W(\omega_j^X)$ is the corresponding weight calculated from a Lorentzian lineshape. With a measured half linewidth of LW, the weight for each frequency component was calculated as:

$$W(\omega_j^X) = \frac{LW^2}{(\Delta\omega_j^X)^2 + LW^2} \tag{10}$$

where $\Delta\omega_j^W$ is the frequency difference between $\omega_j^X$ and the center resonance frequency of metabolite X.

The MRF data from both simulation and experimental studies was processed by applying a Gaussian apodization function to each FID signal to reduce spectral leakage. A Fourier transform was then applied and the spectra phase corrected. As will be described in further detail below, the time courses of the signal from the spectral bins corresponding to one or more of the metabolites was used in parameter matching. In one non-limiting example, three spectral bins corresponding to $P_i$, PCr, and γATP resonances were used in the parameter matching process described below.

In some aspects, determining the one or more metabolite parameter includes iterative parameter estimation using any suitable programming software. In such a procedure, the iterative parameters may include a set number of parameters that are to be matched by, for example, maximizing the magnitude of the $l_2$-normalized inner product between the simulated and the observed signal evolutions. In some aspects, the iterative parameters may include chemical exchange rate constants, concentration ratios, relaxation times, and chemical shift data. In one non-limiting example, the iterative parameters can include 9 parameters, such as the two forward rate constants ($k_f^{CK}$ and $k_f^{ATP}$), the two concentration ratios ($M_R^{PCr}$ and $M_R^{Pi}$), the $T_1$ relaxation time of PCr and $P_i$ ($T_1^{PCr}$ and $T_1^{Pi}$), and the chemical shift of PCr, γATP, and $P_i$ ($\omega^{PCr}$, $\omega^{ATP}$, $\omega^{Pi}$).

In another non-limiting example, a five-step parameter estimation process may be used, with each step optimizing a subset of parameters. In such a method, the resonance frequencies for the one or more metabolites (i.e. $\omega^{PCr}$, $\omega^{ATP}$, $\omega^{Pi}$) are matched using initial values taken from a calibration spectrum. Next, holding $\omega^{PCr}$, $\omega^{ATP}$, and $\omega^{Pi}$ fixed, parameters associated with the creatine kinase system ($k_f^{CK}$, $M_R^{PCr}$, and $T_1^{PCr}$) are matched. This is then followed by the estimation of parameters associated with ATP synthesis from $P_i$ ($k_f^{ATP}$, $M_R^{Pi}$, and $T_1^{Pi}$) while holding the other six parameters constant. Finally, estimation of parameters associated with creatine kinase and ATP synthesis are repeated a second time while holding $\omega^{PCr}$, $\omega^{ATP}$, and $\omega^{Pi}$ constant. In some aspects, the parameter estimation may use a Nelder-Mead Simplex method. In another non-limiting example, parameter estimation is performed with two different sets of randomly chosen initial values to ensure convergence of the matched parameters. $P_i$-to-ATP flux are calculated by multiplying the estimated rate constant $k_f^{ATP}$ with the estimated $P_i$-to-ATP ratio ($M_R^{Pi}$), assuming an ATP concentration of 25.1 μm/g dry weight.

In some aspects, unmatched parameters may be taken from the literature or determined experimentally. The $T_1$ relaxation time of γATP ($T_1^{ATP}$) may be taken from the literature, and the $T_2$ relaxation time of $P_i$, γATP, and PCr ($T_2^{PCr}$, $T_2^{ATP}$, $T_2^{Pi}$) may be obtained experimentally. The linewidth parameter (LW) may be obtained from the calibration spectrum acquired after magnet shimming.

As described above, data acquired with an MRF technique generally includes data containing variable, including random measurements, pseudorandom measurements, or measurements obtained in a manner that results in spatially incoherent signals, temporal incoherent signals, or spatiotemporally incoherent signals. For instance, such data can be acquired by varying acquisition parameters from one TR period to the next, which creates a time series of signals with varying contrast. Using this series of varied sequence blocks simultaneously produces different signal evolutions in different resonant species to which RF energy is applied.

As an example, data are acquired using a pulse sequence where effectuating the pulse sequence includes controlling an NMR apparatus (e.g., an MRI system) to apply RF energy to a volume in an object being imaged. In some aspects, the volume may contain one or more metabolites that comprise $^1H$, $^{13}C$, and $^{31}P$. In other aspects, the volume may include one or more metabolites, such as adenosine triphosphate (ATP), phosphocreatine, inorganic phosphate, N-acetyl aspartate (NAA), lactate, choline, creatine, lipids, myo-inositol, glutamine, glutamate, and the like.

The RF energy may be applied in a series of variable sequence blocks. Sequence blocks may vary in a number of parameters including, but not limited to, echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, and amount of gradient spoiling. Depending upon the imaging or clinical need, two, three, four, or more parameters may vary between sequence blocks. The number of parameters varied between sequence blocks may itself vary. For example, a first sequence block may differ from a second sequence block in five parameters, the second sequence block may differ from a third sequence block in seven parameters, the third sequence block may differ from a fourth sequence block in two parameters, and so on. One skilled in the art will appreciate that there are a very-large number of series of sequence blocks that can be created by varying this large number of parameters. A series of sequence blocks can be crafted so that the series have different amounts (e.g., 1%, 2%, 5%, 10%, 50%, 99%, 100%) of unique sequence blocks as defined by their varied parameters. A series of sequence blocks may include more than ten, more than one hundred, more than one thousand, more than ten thousand, and more than one hundred thousand sequence blocks. In one example, the only difference between consecutive sequence blocks may be the number or parameters of excitation pulses.

Regardless of the particular imaging parameters that are varied or the number or type of sequence blocks, the RF energy applied during a sequence block is configured to cause different individual resonant species to simultaneously produce individual NMR signals. Unlike conventional imaging techniques, in an MRF pulse sequence, at least one member of the series of variable sequence blocks will differ from at least one other member of the series of variable sequence blocks in at least N sequence block parameters, where N is an integer greater than one. One skilled in the art will appreciate that the signal content of a signal evolution may vary directly with N. Thus, as more parameters are varied, a potentially richer signal is retrieved. Conventionally, a signal that depends on a single parameter is desired and required to facilitate imaging. Here, acquiring signals with greater information content facilitates producing more distinct, and thus more matchable, signal evolutions.

The pulse sequence used to acquire the provided data may apply members of the series of variable sequence blocks according to a partially random or pseudo-random acquisition plan configured to undersample the object at an undersampling rate, R. In different situations, the undersampling rate, R, may be, for example, two, four, or greater.

Unlike conventional MRI imaging processes, where the time during which an imaging-relevant NMR signal can be acquired is severely limited (e.g., 4-5 seconds), the NMR apparatus can be controlled to acquire NMR signal for significantly longer periods of time. For example, the NMR apparatus can be controlled to acquire signal for up to ten seconds, for up to twenty seconds, for up to one hundred seconds, or longer. NMR signals can be acquired for longer periods of time because signal information content remains viable for longer periods of time in response to the series of varied RF energy applied. In different situations, the information content in the signal evolution may remain above an information content threshold for at least five seconds, for at least ten seconds, for at least sixty seconds, or for longer. An information content threshold may describe, for example, the degree to which a subsequent signal acquisition includes information that can be retrieved and that differs from information acquired in a previous signal acquisition. For example, a signal that has no retrievable information would likely fall below an information content threshold while a signal with retrievable information that differs from information retrieved from a previous signal would likely be above the information content threshold.

Figure 3:
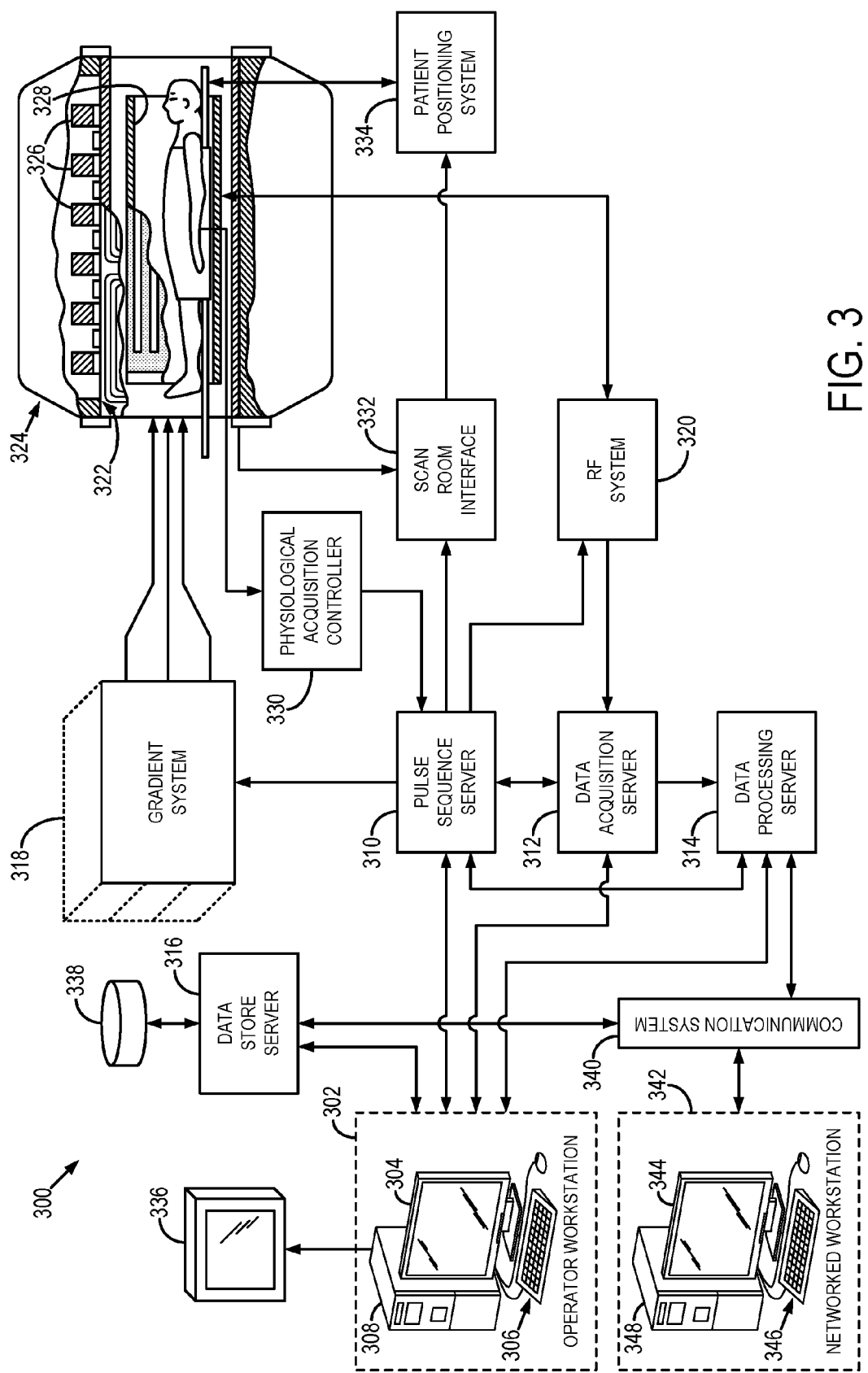
FIG. 3 is a block diagram of an example spectroscopic magnetic resonance fingerprinting ("MRF") system that can implement the methods described in the present disclosure.

Referring particularly now to FIG. 3, an example of an MRI system 300 that can implement the methods described here is illustrated. While the system 300 is described as an MRI system, the systems and methods of the present invention need not provide or use systems designed for imaging. For example, nuclear magnetic resonance (NMR) systems without imaging capabilities may be likewise utilized.

The MRI system 300 includes an operator workstation 302 that may include a display 304, one or more input devices 306 (e.g., a keyboard, a mouse), and a processor 308. The processor 308 may include a commercially available programmable machine running a commercially available operating system. The operator workstation 302 provides an operator interface that facilitates entering scan parameters into the MRI system 300. The operator workstation 302 may be coupled to different servers, including, for example, a pulse sequence server 310, a data acquisition server 312, a data processing server 314, and a data store server 316. The operator workstation 302 and the servers 310, 312, 314, and 316 may be connected via a communication system 340, which may include wired or wireless network connections.

The pulse sequence server 310 functions in response to instructions provided by the operator workstation 302 to operate a gradient system 318 and a radiofrequency ("RF") system 320. Gradient waveforms for performing a prescribed scan are produced and applied to the gradient system 118, which then excites gradient coils in an assembly 322 to produce the magnetic field gradients $G_x$, $G_y$, and $G_z$ that are used for spatially encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil to perform the prescribed magnetic resonance pulse sequence. Responsive magnetic resonance signals detected by the RF coil 328, or a separate local coil, are received by the RF system 320. The responsive magnetic resonance signals may be amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the prescribed scan and direction from the pulse sequence server 310 to produce RF pulses of the desired frequency, phase, and pulse amplitude waveform. The generated RF pulses may be applied to the whole-body RF coil 328 or to one or more local coils or coil arrays.

The RF system 320 also includes one or more RF receiver channels. An RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \tag{11}$$

and the phase of the received magnetic resonance signal may also be determined according to the following relationship:

$$\varphi = \tan^{-1}\left(\frac{Q}{I}\right). \tag{12}$$

The pulse sequence server 310 may receive patient data from a physiological acquisition controller 330. By way of example, the physiological acquisition controller 330 may receive signals from a number of different sensors connected to the patient, including electrocardiograph ("ECG") signals from electrodes, or respiratory signals from a respiratory bellows or other respiratory monitoring devices. These signals may be used by the pulse sequence server 310 to synchronize, or "gate," the performance of the scan with the subject's heart beat or respiration.

The pulse sequence server 310 may also connect to a scan room interface circuit 332 that receives signals from various sensors associated with the condition of the patient and the magnet system. Through the scan room interface circuit 332, a patient positioning system 334 can receive commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, so that data is not lost by data overrun. In some scans, the data acquisition server 312 passes the acquired magnetic resonance data to the data processor server 314. In scans that require information derived from acquired magnetic resonance data to control the further performance of the scan, the data acquisition server 312 may be programmed to produce such information and convey it to the pulse sequence server 310. For example, during pre-scans, magnetic resonance data may be acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also process magnetic resonance signals used to detect the arrival of a contrast agent in a magnetic resonance angiography ("MRA") scan. For example, the data acquisition server 312 may acquire magnetic resonance data and processes it in real-time to produce information that is used to control the scan.

The data processing server 314 receives magnetic resonance data from the data acquisition server 312 and processes the magnetic resonance data in accordance with instructions provided by the operator workstation 302. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 314 are conveyed back to the operator workstation 302 for storage. Real-time images may be stored in a data base memory cache, from which they may be output to operator display 302 or a display 336. Batch mode images or selected real time images may be stored in a host database on disc storage 338. When such images have been reconstructed and transferred to storage, the data processing server 314 may notify the data store server 316 on the operator workstation 302. The operator workstation 302 may be used by an operator to archive the images, produce films, or send the images via a network to other facilities.

The MRI system 300 may also include one or more networked workstations 342. For example, a networked workstation 342 may include a display 344, one or more input devices 346 (e.g., a keyboard, a mouse), and a processor 348. The networked workstation 342 may be located within the same facility as the operator workstation 302, or in a different facility, such as a different healthcare institution or clinic.

The networked workstation 342 may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342.

Further Examples

The following examples set forth, in detail, ways in which the spectroscopic magnetic resonance fingerprinting system 300 may be used or implemented, and will enable one of skill in the art to more readily understand the principles thereof. The following examples are presented by way of illustration and are not meant to be limiting in any way.
Simultaneous Quantification of $T_1$ and $M_0$:

A solution phantom comprised of physiological concentrations of major phosphate metabolites (15 mM PCr, 10 mM ATP, and 3 mM $P_i$) and titrated to 7.1 pH was used for sequence testing. All data acquisitions were performed on a 9.4T vertical bore system (Bruker Biospin Co., Billerica, Mass., USA). The MRF sequence, using a TR of 11.2 ms, was implemented at 11 different carrier frequencies ranged from −8.3 to 5.7 ppm and interspersed at 1 ppm interval. The resonance signals from $P_i$, PCr, γATP and αATP were matched for $T_1$. Classical Inversion Recovery (IR) method was used to compare the accuracy and signal acquisition efficiency of $T_1$ and $M_0$ measurements by MRF. Specifically, a hyperbolic secant inversion pulse was followed by data acquisition at 6 different inversion times ranging from 0.1 to 15 s. A 40 s inter-scan delay was used to reestablish longitudinal magnetization.

The accuracy and measurement efficiency of MRF was further evaluated by comparing the mean of measured $T_1$ and $M_0$ values to those from IR measurements. Three MRF sequences (designated as sequence A, B, and C) that used a specific combination of TR and carrier frequency to place the resonances of $P_i$, PCr, and γATP within the center of either a pass-band or a null-band were evaluated. Sequence A (TR, 12.21 ms TR; carrier frequency, 400 Hz to the left of PCr) placed PCr and Pi within the pass-bands and γATP within a null-band. Sequence B (TR, 13.48 ms; carrier frequency, 445 Hz to the left of PCr) placed all 3 resonances within the pass-bands. Sequence C (TR, 12.35 ms; carrier frequency, 445 Hz to the left of PCr) placed PCr and Pi within the null-bands and γATP within a pass-band. A total of 120 datasets with 1 signal average were acquired for each sequence. For both MRF and IR, measurement efficiency was calculated as:

$$\text{Efficiency} = \frac{\text{Precision}}{\sqrt{\text{Acquisition Time}}}; \quad (13)$$

where precision was determined as the mean to standard deviation ratio. Acquisition time included inter-scan delay time for both MRF and classic IR. For classic IR, calculation of the efficiency assumed an inter-scan delay of 5 times of the $T_1$ of the corresponding metabolite.

For each MRF dataset, a Gaussian filter truncated at 4.4% level was applied to the time domain signal to reduce spectral leakage. The signal was Fourier transformed to spectral domain and the time course of the signal within the spectral bins containing the $P_i$, PCr, γATP, and αATP resonances were used to perform the dictionary matching as described above. For the IR dataset, a 10-Hz line broadening was applied to the FID signal, followed by Fourier transform. For each spectrum, the areas of the resonance peaks corresponding to $P_i$, PCr, γATP, and αATP were determined by integration. $T_1$ and $M_0$ for each species were determined by fitting the data with a 2-parameter exponential model.

$T_1$ measurements by both the classical inversion recovery method (IR) and MRF were obtained. $T_1$ values measured by classical IR method were 7.80, 3.60, 1.76, and 1.32 s for $P_i$, PCr, γATP, and αATP, respectively. For all the 11 carrier frequencies used, MRF-matched $T_1$ values showed strong agreement with that of the classical IR method. The mean and standard deviation for $P_i$, PCr, γATP, and αATP were 7.40±0.54, 3.48±0.06, 1.74±0.05, and 1.26±0.11 s, respectively. These results suggest that spectroscopic MRF can be applied to simultaneously measure $T_1$ of multiple metabolites over a wide range of carrier frequencies.

The measurement efficiency showed a 46% to 146% improvement for pass-band PCr and γATP resonances. It is important to note that this improvement by MRF was substantially underestimated by the hardware limitations of our current system. Specifically, the required data writing time to system RAM after each acquisition (~5 ms for our current hardware) reduced the data acquisition window to only 6 ms within each TR (11 ms). Second, after the 7 s acquisition of each fingerprint, an inter-scan delay of 8 seconds was required for writing the acquired data to the hard disk. These hardware limitations lead to substantial loss of acquisition efficiency in our current study. In addition, the memory size of the system limited the maximum number of acquisitions for each fingerprint to 512, leading to incomplete coverage of signal evolution for long $T_1$ species such as $P_i$ in vitro.

The chemical shift difference of major phosphate metabolites gave rise to a spectral bandwidth that is two-orders of magnitude wider than those typically encountered in proton imaging. To maintain sensitivity for all the metabolites, the current pulse sequence used a constant TR with small ramped flip angles to obtain a bSSFP-like frequency response such that with an appropriately chosen carrier frequency and TR, resonance peaks could be placed within different pass-bands. With the relatively homogenous frequency response within an individual pass-band region and the relatively low flip angles, signal evolution was insensitive to $T_2$, chemical shift, $B_0$ and $B_1$ inhomogeneity, and inaccuracies in $B_1$ calibration, as was manifested in the consistency in $T_1$ matching. Like the spectroscopic bSSFP methods, placing resonance peaks in pass-bands requires a priori knowledge of the chemical shift of all the metabolites.

Our current implementation using constant TR and linearly ramped flip angle trains differed significantly from the proton MRF methods that used randomly varying TR and flip angles. Monte Carlo simulation shows that adding randomness to ramped flip angle train yielded similar accuracy and precision for $T_1$ and $M_0$ measurements under all conditions examined. While random TR showed similar precision as constant TR for on-resonance metabolites, it exhibited large matching inaccuracy and decreased precision in the far off-resonance case. These results suggest that randomness in pulse sequence parameters does not guarantee optimal parameter sensitivity and accuracy.

To reduce spectral leakage, a Gaussian filter was applied to each FID signal before Fourier transform to the spectral domain. This filtering effectively redistributed spectral energy to primarily the central and two adjacent spectral bins of a resonance peak. In the present disclosure, the real and imaginary components of signal evolution in all three spectral bins were predicted by Bloch simulation combined with the same Gaussian filter. Template matching was then performed simultaneously to signals in all three spectral bins. This approach deviated from most classic methods of spectral quantification that frequently involved operator-dependent phasing and curve fitting. As long as metabolite peaks resolve, quantification and matching of a fingerprint for a specific metabolite are accurate and independent of other metabolites. As such, nuclei with large chemical shift dispersion, such as $^{31}P$ and $^{13}C$, are good candidate nuclei for spectroscopic MRF.

MRF Method for Fast Quantification of the Chemical Exchange Rates:

In vivo studies were performed to assess the accuracy of the CK-MRF measurements in rat hindlimb. Briefly, three-month-old Sprague-Dawley rats (n=17) were anesthetized and positioned laterally in a cradle. The hindlimb was secured within a 15-mm $^{31}P$ coil placed within a $^1H$ volume coil and positioned at the isocenter of a 9.4T MRI scanner (Bruker Biospin Co., Billerica, Mass.). An air pressure cuff was placed proximal to the coil. Body temperature was maintained at above 35° C. via a feedback control system (SA Instruments, Stony Brook, N.Y., USA). The respiratory rate was maintained between 45 and 60 breaths per minute by manually adjusting the anesthesia level. The animal protocol was approved by the Institutional Animal Care and Use Committee of Case Western Reserve University.

Following initial stabilization, shimming, and $B_1$ power calibrations, CK-MRF and MT-MRS data were acquired at baseline. Due to their substantially different acquisition times for a single-average dataset (20 s for CK-MRF versus 150 s for MT-MRS), 24 repetitions of CK-MRF data (8 min acquisition) and 4 repetitions of MT-MRS data (10 min acquisition) were acquired in an interleaved manner. A total of 96 repetitions of CK-MRF data and 12 repetitions of MT-MRS data were acquired. 14 rats subsequently underwent two rounds of ischemia/reperfusion (IR) before a second data collection session. Ischemia was induced by inflating the cuff to above 200 mmHg and lasted for 17 min. The ischemic period was followed by 17 minutes of reperfusion. At the end of the IR protocol, another session of data collection started, in which a total of 48 repetitions of CK-MRF data and 8 repetitions of MT-MRS data were acquired.

The remaining three rats were used as the controls. They underwent the same data collection sessions, separated by a 70-min period, during which CK-MRF and FAST data were collected. Acquisition of 24 repetitions of CK-MRF data and 120 repetitions of FAST data were interleaved. A total of 96 and 480 repetitions were collected for the CK-MRF and FAST methods, respectively.

The FAST acquisition consisted of 4 spectra acquired with either 15° or 60° F.A, and with either γATP or control saturation. A BIR-4 pulse was used for excitation. All the spectra were acquired after five dummy scans with a TR of 1 s. Parameter estimation of $k_f^{CK}$, $T_1^{PCr}$, and $M_R^{PCr}$ for FAST data was performed using the established closed-form derivation.

MT-MRS acquisition consisted of 9 spectra: 7 spectra acquired after γATP saturation, with saturation times of 0.4, 0.9, 1.3, 2.2, 3.5, 5.3 and 7 s, respectively; a control spectrum with contralateral saturation; and a conventional spectrum without saturation. All spectra were acquired using 90° excitation and a 16 s TR. Post-processing consisted of 15 Hz line broadening, Fourier transform, and correction of phase and baseline. The signal intensity from PCr was quantified by integrating the area under the PCr peak. Subsequently, $k_f^{CK}$, $T_1^{PCr}$, and $M_0^{PCr}$ were determined by fitting the explicit solution of the Bloch-McConnell equation to the experimental data. Effects of RF spillover were corrected using the method outlined by Kingsley et al. Table 1 below shows group statistics for in vivo data that compares conventional methods with CK-MRF. The CK-MRF method shows an improved acquisition time and efficiency compared to conventional methods, as demonstrated by in vivo experiments. In the current study, CK-MRF was able to measure $k_f^{CK}$ in vivo in 20 seconds with a coefficient of variation of only 4%, while conventional MT-MRS required 150 s and had a CV of 9%.

TABLE 1

Summary of Measured Parameter Values Pre-IR and Post-IR

| | | Signal Averages | $k_f^{CK}$ (s$^{-1}$) | $T_1^{PCr}$ (s) | $M_R^{PCr}$ |
|---|---|---|---|---|---|
| Pre-IR | MT-MRS | 12 | 0.39 ± 0.03 | 3.49 ± 0.11 | 4.22 ± 0.20 |
| | CK-MRF | 96 | 0.38 ± 0.02* | 3.54 ± 0.11 | 4.16 ± 0.19 |
| Post-IR | MT-MRS | 8 | 0.44 ± 0.04† | 3.48 ± 0.19 | 4.11 ± 0.30 |
| | CK-MRF | 48 | 0.42 ± 0.03 | 3.49 ± 0.13 | 4.07 ± 0.19† |

MRF-based Magnetization Transfer Encoding Method (MT-MRF):

Both in vitro and in vivo studies were performed on a horizontal 9.4T Bruker Biospec scanner (Bruker Biospin Co., Billerica, Mass., USA). The MT-MRF pulse sequence and quantification method were first validated in vitro. A single compartment phantom composed of 150 mM PCr, 100 mM ATP, and 60 mM $K_2HPO_4$ was used for in vitro validation. MT-MRF data were acquired with 20 signal averages. Matched parameters were compared to those obtained from conventional MT-IR.

The conventional inversion-recovery MT (MT-IR) method was used for all comparison studies below. The same set of MT-IR acquisition parameters was used for both simulation studies and experimental validations. Specifically, after the inversion pulse, continuous wave γATP saturation of 0.1, 0.6, 1.2, 2.5, 5, 10, and 18 s was applied before data acquisition. An inter-scan delay of 18 s was used to allow complete magnetization recovery. Each FID consisted of 2148 data points acquired at 74 µs dwell time. A control spectrum was acquired with the frequency of the saturation pulse set downfield of Pi symmetric to γATP.

In the phantom study, parameter matching using the MT-MRF method was in good agreement with the conventional MT-IR method. Both methods yielded a $k_f^{ATP}$ value of 0.00 s$^{-1}$, reflecting the absence of enzymes for ATP synthesis. Estimation of $k_f^{CK}$ was also 0.00 s$^{-1}$ from both methods, reflecting the absence of creatine kinase. Estimated $T_1^{Pi}$ was 3.86 s using the MT-MRF method and 3.82 s using the MT-IR method, and $P_i$-to-ATP ratio was 1.36 and 1.32 using MT-MRF and MT-IR, respectively.

Four-month old male Sprague-Dawley rats (n=7) were anesthetized with 1.5-2.5% isoflurane and positioned laterally in a cradle. The left hind limb was secured within an in-house built 20-mm $^{31}$P saddle coil placed within a $^1$H volume coil and at the isocenter of the magnet. Body temperature was maintained at above 35° C. by blowing warm air into the scanner via a feedback control system (SA Instruments, Stony Brook, N.Y.). The respiratory rate was maintained at about 30 breaths per minute by adjusting the anesthesia level. The animal protocol was approved by the Institutional Animal Care and Use Committee of Case Western Reserve University.

Automatic, localized shimming was performed on a volume of 15 mm$^3$ that covered the entire calf muscle using a PRESS sequence. Calibration $^{31}$P spectra were acquired to determine the linewidth and the resonance frequencies of the metabolites. After all calibrations were completed, MT-MRF and MT-IR data were acquired alternately, with each acquisition lasting for 10 minutes. Total acquisition time was 200 min, with 10 acquisition sessions for each method. Because of the shorter MRF acquisition time, 18 signal averages were acquired for MT-MRF while 3 signal averages were acquired for MT-IR for each of the 10-min acquisition session.

For parameter estimation, signal averaging equivalent to 30-min acquisition was obtained by averaging 3 consecutive acquisition sessions for each method, yielding 54 signal averages for MT-MRF and 9 signal averages for MT-IR. To assess the agreement between MT-MRF and MR-IR methods, 100-min signal averaging was also obtained by using all 10 datasets for each method.

The mean and standard deviation for all in vivo measurements are summarized in Table 2. These values were within the range of previously reported literature values for resting rat skeletal muscle measured by conventional $^{31}$P-MRS methods.

TABLE 2

Parameter estimation in rat hind limb with 30-min and 100-min data acquisition.

|  |  | $k_f^{ATP}$ (s$^{-1}$) | $T_1^{Pi}$ (s) | Pi-to-ATP Ratio | Pi-to-ATP Flux (□mol/s/g dw) |
|---|---|---|---|---|---|
| MT-IR | 30-min acq | 0.081 ± 0.056 | 5.77 ± 2.07 | 0.27 ± 0.05 | 0.57 ± 0.45 |
|  | 100-min acq | 0.075 ± 0.024 | 5.70 ± 0.65 | 0.26 ± 0.02 | 0.48 ± 0.16 |
| MT-MRF | 30-min acq | 0.085 ± 0.035 | 5.23 ± 1.00 | 0.26 ± 0.05 | 0.55 ± 0.23 |
|  | 100-min acq | 0.083 ± 0.021 | 5.06 ± 0.52 | 0.26 ± 0.05 | 0.53 ± 0.14 |

MT-MRF and MT-IR yielded similar mean values for the estimation of $k_f^{ATP}$, $T_1^{Pi}$, and the $P_i$-to-ATP ratio. As a result, calculated $P_i$-to-ATP flux was also similar. Comparing to parameter estimation by MT-IR, MT-MRF showed significantly smaller variation in the estimation of $k_f^{ATP}$ and $T_1^{Pi}$ ($p<0.05$), as well as the calculated $P_i$-to-ATP flux ($p<0.05$).

The MT-MRF pulse sequence as disclosed gave rise to a biphasic signal evolution that allowed more sensitive differentiation of the enzymatic rates. In combination with an acquisition scheme that maximized SNR with minimal perturbation of the longitudinal magnetization, the MT-MRF method allowed more efficient measurement of the ATP synthesis rate than the conventional MT-IR method in both simulation studies and in vivo experiments.

Parameter estimation by the MT-MRF method was shown to be accurate and robust to varied experimental conditions and physiological parameters. None of the errors in the unmatched parameters caused discontinuities in parameter matching, suggesting robust pulse sequence design, as well as convergence stability of the parameter estimation method.

A constant TR and a regular flip angle pattern were used in the current study, which differed from previous proton MRF methods that used randomly varying TR and flip angles. A constant TR of 7.7 ms was used so that the accumulated phase of $P_i$, PCr, and γATP would all be an integer multiple of 360° during each TR, which allowed the refocusing of the transverse magnetization and thus improved SNR. A regular flip angle pattern was used because preliminary simulation results using random flip angle patterns did not show improvements in parameter estimation (data not shown).

The present disclosure has described one or more preferred embodiments, and it should be appreciated that many equivalents, alternatives, variations, and modifications, aside from those expressly stated, are possible and within the scope of the invention.

The invention claimed is:

1. A method for performing phosphorous spectroscopic magnetic resonance fingerprinting (MRF) comprising:
    performing a pulse sequence using a series of varied sequence blocks to simultaneously produce different signal evolutions from different resonant species in a volume in a subject, wherein at least one member of the series of varied sequence blocks differs from at least one other member of the series of varied sequence blocks in at least N sequence block parameters, where N is an integer greater than one and wherein the different resonant species include one or more metabolites;
    acquiring MRF data as the series of different signal evolutions from different resonant species in the volume in the subject;
    determining parameters associated with phosphate metabolites and chemical exchange rates between these metabolites by comparing the MRF data to a simulated MRF signal; and
    identifying metabolic alterations in the subject based on the determined parameters.

2. The method of claim 1 wherein the metabolite parameter includes quantifying the concentration ($M_0$) of at least one of the one or more metabolites.

3. The method of claim 1 wherein the metabolite parameter includes quantifying a rate constant for at least one of the one or more metabolites.

4. The method of claim 3 wherein the rate constant includes a forward ATP rate constant ($k_f^{ATP}$).

5. The method of claim 1 wherein performing a pulse sequence using a series of varied sequence blocks includes using a constant repetition time (TR).

6. The method of claim 1 wherein using a series of varied sequence blocks includes using linearly ramped flip angles.

7. The method of claim 1 wherein the simulated MRF signal includes signals correlated to at least one known metabolite parameter for the one or more metabolites.

8. The method of claim 1 wherein the one or more metabolites include phosphorus-31 ($^{31}P$).

9. The method of claim 8 wherein the one or more metabolites is selected from the group consisting of inorganic phosphate, phosphocreatine (PCr), adenosine triphosphate (ATP), adenosine diphosphate, and creatine.

10. The method of claim 1 wherein the pulse sequence is a hyperbolic secant inversion pulse.

11. A method for performing phosphorous spectroscopic magnetic resonance fingerprinting (MRF) comprising:
   performing a pulse sequence using a series of varied sequence blocks to a volume in a subject, the volume containing one or more metabolites;
   acquiring a series of signal evolutions from the volume in the subject to form MRF data;
   determining parameters associated with phosphate metabolites and chemical exchange rates between these metabolites by comparing the MRF data to simulated MRF signal; and
   identifying metabolic alterations in the subject based on the determined parameters;
   wherein the simulated MRF signal includes signals correlated to at least one known metabolite parameter for the one or more metabolites; and
   wherein the at least one known metabolite parameter includes chemical shift data and a range of longitudinal relaxation times ($T_1$).

12. A method for performing phosphorous spectroscopic magnetic resonance fingerprinting (MRF) comprising:
   performing a pulse sequence using a series of varied sequence blocks to a volume in a subject, the volume containing one or more metabolites;
   acquiring a series of signal evolutions from the volume in the subject to form MRF data;
   determining parameters associated with phosphate metabolites and chemical exchange rates between these metabolites by comparing the MRF data to simulated MRF signal;
   identifying metabolic alterations in the subject based on the determined parameters; and
   characterizing the one or more metabolites by assigning the MRF data associated with the one or more metabolites to at least one spectral bin.

13. A method for performing phosphorous spectroscopic magnetic resonance fingerprinting (MRF) comprising:
   performing a pulse sequence using a series of varied sequence blocks to a volume in a subject, the volume containing one or more metabolites;
   acquiring a series of signal evolutions from the volume in the subject to form MRF data;
   determining parameters associated with phosphate metabolites and chemical exchange rates between these metabolites by comparing the MRF data to simulated MRF signal;
   identifying metabolic alterations in the subject based on the determined parameters; and
   wherein comparing the MRF data to the simulated MRF signal includes taking a dot product between the at least one known metabolite parameter in the simulated MRF signal and the MRF data in the at least one spectral bin.

14. A method for performing phosphorous spectroscopic magnetic resonance fingerprinting (MRF) comprising:
   performing a pulse sequence using a series of varied sequence blocks to a volume in a subject, the volume containing one or more metabolites;
   acquiring a series of signal evolutions from the volume in the subject to form MRF data;
   determining parameters associated with phosphate metabolites and chemical exchange rates between these metabolites by comparing the MRF data to simulated MRF signal; and
   identifying metabolic alterations in the subject based on the determined parameters;
   wherein identifying the metabolic alternations includes generating a matched fingerprint; and
   wherein the matched fingerprint is the highest dot product between the acquired MRF data and simulated MRF signal with predefined metabolite parameters.

15. The method of claim 14 wherein the at least one metabolite parameter is $T_1$.

16. The method of claim 15 where the $M_0$ of the one or more metabolites is subsequently determined by minimizing the error term using the following equation:

$$\Sigma |S - M_0 D|$$

wherein S is the MRF data and D is the matched fingerprint.

17. A method for performing spectroscopic magnetic resonance fingerprinting (MRF) comprising:
   performing a pulse sequence using a series of varied sequence blocks to simultaneously produce different signal evolutions from different resonant species in a volume in an object, the volume containing one or more metabolites;
   acquiring the simultaneously produced different signal evolutions from different resonant species to form MRF data, wherein the signal evolutions are positioned in a pass-band;
   characterizing the one or more metabolites by comparing one of the signal evolutions from the MRF data to a simulated MRF signal, wherein comparing including performing signal template matching to select a set of values from the simulated MRF signal that correspond to the signal evolution from the MRF data; and
   determining at least one metabolite parameter based at least in part on the selected set of values from the simulated MRF signal.

18. The method of claim 17 wherein determining the at least one metabolite parameter for the one or more metabolites includes generating a matched fingerprint.

19. A method for performing spectroscopic magnetic resonance fingerprinting (MRF) comprising:
   performing a pulse sequence using a series of varied sequence blocks to a volume in an object, the volume containing one or more metabolites;
   acquiring a series of signal evolutions from the volume in the object to form MRF data, wherein the signal evolutions are positioned in a pass-band;
   characterizing the one more metabolites by comparing the MRF data to simulated MRF signal;
   determining at least one metabolite parameter; and
   wherein positioning the signal evolution within the pass-band includes varying the carrier frequency and TR.

20. A system comprising:
   a magnet system configured to generate a polarizing magnetic field about at least a portion of a subject;
   a magnetic gradient system including a plurality of magnetic gradient coils configured to apply at least one magnetic gradient field to the polarizing magnetic field;
   a radio frequency (RF) system configured to apply an RF field to the subject and to receive magnetic resonance signals from the subject using a coil array;
   a computer system programmed to:
      control the magnetic gradient system and the RF system to perform a pulse sequence using a series of varied sequence blocks to elicit different signal evolutions from different resonant species in a volume in a subject containing one or more metabolites, wherein at least one member of the series of varied sequence blocks differs from at least one other member of the series of varied sequence blocks in at least N sequence block parameters, where N is an integer greater than one; and acquire a series of the signal evolutions from the volume to form MRF data, wherein the signal evolutions are positioned in a pass-band;

characterize the one or more metabolites by comparing one of the signal evolutions from the MRF data to a simulated MRF signal wherein comparing including performing signal template matching to select a set of values from the simulated MRF signal that correspond to the signal evolution from the MRF data; and generate a report indicating at least the one or more metabolites.

* * * * *